United States Patent [19]

Dutra et al.

[11] 4,322,239

[45] Mar. 30, 1982

[54] N-NITROSO-N-PHOSPHONOMETHYLGLYCINE ESTERS AND THE HERBICIDAL USE THEREOF

[75] Inventors: Gerard A. Dutra, Ladue, Mo.; James A. Sikorski, West Lafayette, Ind.

[73] Assignee: Monsanto Company, St. Louis, Mo.

[21] Appl. No.: 177,677

[22] Filed: Aug. 13, 1980

[51] Int. Cl.³ .......................... A01N 57/18; C07F 9/40
[52] U.S. Cl. .......................................... 71/86; 260/923
[58] Field of Search ............................ 260/923; 71/86

[56] References Cited

U.S. PATENT DOCUMENTS

| | | | |
|---|---|---|---|
| 3,888,915 | 6/1975 | Alt | 71/86 |
| 3,979,200 | 9/1976 | Alt | 71/86 |
| 4,008,296 | 2/1977 | Barton | 260/940 |
| 4,120,689 | 10/1978 | Dutra | 260/944 |

*Primary Examiner*—Anton H. Sutto
*Attorney, Agent, or Firm*—Gordon F. Sieckmann; Howard C. Stanley

[57] ABSTRACT

This disclosure relates to N-nitroso-N-phosphonomethylglycine triesters and their use as herbicides and in herbicidal compositions. More particularly, this disclosure relates to N-nitroso-N-phosphonomethylglycine esters wherein a lower alkyl or benzyl group is bonded to the carboxyl moiety and a phenyl or substituted phenyl group is bonded to phosphorus.

24 Claims, No Drawings

N-NITROSO-N-PHOSPHONOMETHYLGLYCINE ESTERS AND THE HERBICIDAL USE THEREOF

This invention relates to N-nitroso-N-phosphonomethylglycine compounds. More particularly, this invention relates to N-nitroso-N-phosphonomethylglycine triesters, their use in herbicidal compositions and their use as herbicides.

The N-nitroso-N-phosphonomethylglycine compounds of this invention are those having the formula

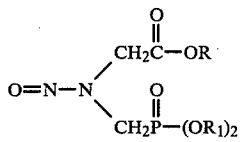

wherein R is a member of the class consisting of lower alkyl or benzyl and $R_1$ is a member of the class consisting of phenyl and lower alkoxy substituted phenyl groups.

The term "lower alkyl" as employed herein encompasses straight and branched chain alkyl groups containing from 1 to 4 carbon atoms, for example, methyl, ethyl, isopropyl, t-butyl and the like.

The term "lower alkoxy" as employed herein is the straight and branched chain alkoxy groups containing from 1 to 4 carbon atoms, e.g., methoxy, ethoxy, propoxy and butoxy. Preferably, the alkoxy groups are primary or secondary alkoxy groups.

Illustrative of the lower alkoxy substituted phenyl groups represented by $R_1$ are, for example, o-, m- and p-methoxyphenyl; o-, m- and p-ethoxyphenyl; o-, m- and p-propoxyphenyl and the like.

The compounds of the instant invention are produced by the reaction of a triester of N-phosphonomethylglycine or a strong acid salt thereof having the formula

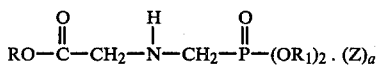

wherein R and $R_1$ have the above-defined meanings, Z is a strong acid and (a) is 0 or 1 with an alkali metal or alkaline earth metal nitrite in the presence of a hydrohalic acid at a temperature of from $-10°$ to $35°$ C.

The strong acids that Z represent are those having a pKa in water of 2.2 or less, for example, methane sulfonic acid, hydrochloric, trifluoroacetic, hydrobromic, hydroiodic, sulfuric, trichloroacetic, chlorosulfonic, benzenesulfonic, trifluoromethanesulfonic and the like.

In conducting the process of the instant invention, the ratio of the metal nitrite to the N-phosphonomethylglycine triester is not narrowly critical and can be varied over a wide range, i.e., from about 1:10 to 10:1. It is, of course, preferred to employ the metal nitrite in excess to insure completeness of reaction and allow for easier isolation of the desired product.

The temperature at which the process is conducted can vary from about $-10°$ C. to $35°$ C. or even higher. It is preferred for convenience to conduct the process at from about 5° C. to about 15° C.

The compounds and compositions of the present invention find use as herbicides.

The following examples serve to further illustrate the invention. All parts are parts by weight unless otherwise expressly set forth.

EXAMPLE 1

(Bis(2-methoxyphenoxy)phosphinylmethyl)glycine, ethyl ester, (10 g; 0.024 mol) was added to a solution of concentrated hydrochloric acid (20 ml.) in water (20 ml.) and cooled to 10° C. The resulting solution was stirred for 15 minutes and then aqueous sodium nitrite was added (4.14 g in 20 ml. of water) dropwise. An immediate reaction took place and an orange-colored oil formed. When the addition was complete, the mixture was stirred at 0° C. for 1 hour. The aqueous layer was then decanted and the insoluble oil remaining was washed with water several times and then dissolved in approximately 200 ml. of methylene chloride and washed with water, aqueous potassium carbonate and finally with water. The methylene chloride layer was separated, dried over magnesium sulfate and then concentrated to yield a dark red oil. The dark red oil was concentrated under vacuum for 2 hours to remove the remaining traces of methylene chloride. The resulting red oil ($n_D^{25} 1.5140$) was (bis(2-methoxyphenoxy)phosphinylmethyl)-N-nitrosoaminoglycine, ethyl ester, having the following analysis:

Calculated: C, 52.06; H, 5.29; N, 6.39. Found: C, 51.82; H, 5.34; N, 6.28.

EXAMPLE 2

N-((diphenoxyphosphinyl)methyl)glycine, methyl ester, methane sulfonic acid salt, (5.0 g; 0.011 mol) was reacted with sodium nitrite in accordance with the procedure of Example 1 to produce N-(di(diphenoxyphosphinyl)-methyl)-N-nitroso-glycine, methyl ester, as a dark orange oil, $n_D^{25} = 1.5475$ and having the following analysis:

Calculated: C, 52.75; H, 4.70; N, 7.69. Found: C, 52.79; H, 4.71; N, 7.67.

EXAMPLE 3

N-(di(4-methoxyphenoxyphosphinyl)methyl)glycine, methyl ester, (6 g; 0.0146 mol) was reacted with sodium nitrite in accordance with the procedure of Example 1 to yield N-(di(4-methoxyphenoxyphos-phinyl)methyl)-N-nitriso-glycine, methyl ester, as a brown oil, $n_D^{26}.2 = 1.5483$, and having the following analysis:

Calculated: C, 50.95; H, 4.99; P, 7.30. Found: C, 50.90; H, 5.12; P, 7.43.

EXAMPLE 4

N-(di(phenoxyphosphinyl)methyl)glycine, benzyl ester, methane sulfonic acid salt (10.5 g; 0.02 mol) was reacted with sodium nitrite in accordance with the procedure of Example 1 to yield N-(di(phenoxyphosphinyl)methyl)-N-nitroso-glycine as an oil, $n_D^{25} = 1.5545$ which crystallized on standing to a solid at a melting point of 40°–44° C. and having the following analysis:

Calculated: C, 60.00; H, 4.81; N, 6.36. Found: C, 59.90; H, 4.87; N, 6.33.

EXAMPLE 5

The post-emergence herbicidal activity of the various compounds of this invention is demonstrated by greenhouse testing in the following manner. A good grade of top soil is placed in aluminum pans having holes in the bottom and compacted to a depth of 0.95 to 1.27 cm.

from the top of the pan. A predetermined number of seeds of each of several dicotyledonous and monocotyledonous annual plant species and/or vegetative propagules for the perennial plant species are placed on the soil and pressed into the soil surface. The seeds and/or vegetative propagules are covered with soil and leveled. The pans are then placed on a sand bench in the greenhouse and watered from below as needed. After the plants reach the desired age (two to three weeks), each pan except for the control pans is removed individually to a spraying chamber and sprayed by means of an atomizer operating at a positive air pressure of approximately 1.46 kg/cm$^2$ absolute. The atomizer contains 6 ml. of a solution or suspension of the chemical. In that The plant species utilized in these tests are identified by letter in accordance with the following legend:

| | |
|---|---|
| A - Canada Thistle* | K - Barnyardgrass |
| B - Cocklebur | L - Soybean |
| C - Velvetleaf | M - Sugar Beet |
| D - Morningglory | N - Wheat |
| E - Lambsquarters | O - Rice |
| F - Smartweed | P - Sorghum |
| G - Yellow Nutsedge* | Q - Wild Buckwheat |
| H - Quackgrass* | R - Hemp Sesbania |
| I - Johnsongrass* | S - Panicum Spp |
| J - Downy Brome | T - Crabgrass |

*Established from vegetative propagules.

TABLE I

| Compound of Example No. | WAT | kg/h | A | B | C | D | E | F | G | H | I | J | K |
|---|---|---|---|---|---|---|---|---|---|---|---|---|---|
| 1 | 4 | 11.2 | 1 | 2 | 0 | 1 | 1 | 3 | 1 | 1 | 3 | 1 | 3 |
| 1 | 4 | 5.6 | 1 | 1 | 0 | 1 | 1 | 0 | 0 | 0 | 1 | 0 | 2 |
| 2 | 4 | 11.2 | 2 | 3 | 3 | 2 | 3 | 4 | 1 | 2 | 2 | 1 | 2 |
| 2 | 4 | 5.6 | 2 | 2 | 2 | 2 | 1 | 3 | 1 | 1 | 2 | 1 | 2 |
| 3 | 4 | 11.2 | 2 | 3 | 3 | 2 | 3 | 4 | 0 | 1 | 1 | 2 | 3 |
| 3 | 4 | 5.6 | 1 | 2 | 1 | 2 | 4 | 4 | 1 | 1 | 0 | 1 | 2 |
| 4 | 4 | 11.2 | — | 1 | 1 | 2 | 3 | 0 | 1 | 1 | 1 | 0 | 3 |
| 4 | 4 | 5.6 | — | 1 | 0 | 1 | 2 | 0 | 1 | 1 | 3 | 0 | 2 |

TABLE II

| Compound of Example No. | WAT | kg/h | L | M | N | O | P | B | Q | D | R | E | F | C | J | S | K | T |
|---|---|---|---|---|---|---|---|---|---|---|---|---|---|---|---|---|---|---|
| 1 | 4 | 5.6 | 1 | 4 | 2 | 1 | 3 | 3 | 2 | 2 | 2 | 4 | 3 | 1 | 2 | 4 | 3 | 3 |
| 1 | 4 | 1.12 | 1 | 1 | 1 | 1 | 1 | 2 | 1 | 2 | 0 | 0 | 0 | 1 | 0 | 3 | 2 | 2 |
| 2 | 4 | 5.6 | 2 | 3 | 2 | 3 | 2 | 2 | 1 | 3 | 2 | 2 | 4 | 3 | 1 | 4 | 3 | 3 |
| 2 | 4 | 1.12 | 1 | 1 | 1 | 0 | 1 | 1 | 0 | 2 | 0 | 1 | 0 | 1 | 1 | 2 | 2 | 2 |
| 3 | 4 | 5.6 | 1 | 4 | 2 | 1 | 2 | 3 | 3 | 3 | — | 3 | 3 | 3 | 2 | 3 | 3 | 3 |
| 3 | 4 | 1.12 | 1 | 1 | 1 | 1 | 1 | 2 | 0 | 2 | 4 | 3 | 4 | 1 | 0 | 2 | 1 | 2 |
| 4 | 4 | 5.6 | 1 | 1 | 2 | 0 | 2 | 2 | 2 | 2 | 1 | 2 | 2 | 2 | 1 | 3 | 2 | — |
| 4 | 4 | 1.12 | 1 | 0 | 1 | 0 | 0 | 0 | 0 | 1 | 0 | 0 | 0 | 1 | 0 | 2 | 1 | — |

6 ml is an amount of a cyclohexanone emulsifying agent mixture to give a spray solution or suspension which contains about 0.4% by weight of the emulsifier. The spray solution or suspension contains a sufficient amount of the candidate chemical in order to give application rates corresponding to those set forth in the tables. The spray solution is prepared by taking an aliquot of a 1.0% by weight stock solution or suspension of the candidate chemical in an organic solvent such as acetone or tetrahydrofuran or in water. The emulsifying agent employed is a mixture comprising 35 weight percent butylamine dodecylbenzene sulfonate and 65 weight percent of a tall oil ethylene oxide condensate having about 11 moles of ethylene oxide per mole of tall oil. The pans are returned to the greenhouse and watered as before and the injury to the plants as compared to the control is observed at approximately two and four weeks as indicated in the tables under WAT and the results recorded. In some instances, the two-week observations are omitted.

The post-emergence herbicidal activity index used in Tables I and II is as follows:

| Plant Response | Index |
|---|---|
| 0-24% control | 0 |
| 25-49% control | 1 |
| 50-74% control | 2 |
| 75-99% control | 3 |
| 100% control | 4 |

From the test results presented in Tables I and II, it can be seen that the post-emergent herbicidal activity of the compounds of this invention is, for the most part, general in nature. In certain specific instances, however, some selectivity is demonstrated. In this regard it should be recognized that each individual species selected for the above tests is a representative member of a recognized family of plant species.

The herbicidal compositions, including concentrates which require dilution prior to application to the plants, of this invention contain from 5 to 95 parts by weight of at least one compound of this invention and from 5 to 95 parts by weight of an adjuvant in liquid or solid form, for example, from about 0.25 to 25 parts by weight of wetting agent, from about 0.25 to 25 parts by weight of a dispersant and from 4.5 to about 94.5 parts by weight of inert liquid extender, e.g., water, acetone, tetrahydrofuran, all parts being by weight of the total composition. Preferably, the compositions of this invention contain from 5 to 75 parts by weight of at least one compound of this invention, together with the adjuvants. Where required, from about 0.1 to 2.0 parts by weight of the inert liquid extender can be replaced by a corrosion inhibitor such as ethanol mercaptan, sodium thiosulfate, dodecylmono or dimercaptan or anti-foaming agent such as a dimethylpolysiloxane, or both. The compositions are prepared by admixing the active ingredient with an adjuvant including diluents, extenders, carriers and conditioning agents to provide compositions in the form of finely-divided particulate solids, pellets, solutions, dispersions or emulsions. Thus, the active ingredient can be used with an adjuvant such as a finely-divided solid, a liquid of organic origin, water, a wetting agent, a dispersing agent, an emulsifying agent or any suitable combination of these.

The herbicidal compositions of this invention, particularly liquids and soluble powders, preferably contain as a conditioning agent one or more surface-active agents in amounts sufficient to render a given composition readily dispersible in water or in oil. The incorporation of a surface-active agent into the compositions greatly enhances their efficacy. By the term "surface-active agent", it is understood that wetting agents, dispersing agents, suspending agents and emulsifying agents are included therein. Anionic, cationic and non-ionic agents can be used with equal facility.

Preferred wetting agents are alkyl benzene and alkyl naphthalene sulfonates, sulfated fatty alcohols, amines or acid amides, long chain acid esters of sodium isothionate, esters of sodium sulfosuccinate, sulfated or sulfonated fatty acid esters petroleum sulfonates, sulfonated vegetable oils, polyoxyethylene derivatives of phenols and alkylphenols (particularly isooctylphenol and nonylphenol) and polyoxyethylene derivatives of the mono-higher fatty acid esters of hexitol anhydrides (e.g., sorbitan). Preferred dispersants are methyl cellulose, polyvinyl alcohol, sodium lignin, sulfonates, polymeric alkyl naphthalene sulfonates, sodium naphthalene sulfonate, polymethylene bisnaphthalenesulfonate and sodium N-methyl-N-(long chain acid) taurates.

The following list gives some specific herbicidal compositions of this invention. It is to be realized that the solvents and surfactants are interchangeable in the composition.

| | |
|---|---|
| 1. (Bis(2-methoxyphenoxy)phosphinyl-methyl)-N-nitrosoamino-glycine, ethyl ester | 95 parts |
| Methanol | 5 parts |
| 2. N-((diphenoxyphosphinyl)methyl)-N-nitroso-glycine, methyl ester | 95 parts |
| Ethoxylated nonyl phenol | 5 parts |
| 3. N-(di(4-methoxyphenoxyphosphinyl)-methyl)-N-nitroso-glycine, methyl ester | 90 parts |
| Isopropanol | 10 parts |
| 4. N-(di(phenoxyphosphinyl)methyl)-N-nitroso-glycine | 90 parts |
| Ethoxylated octyl phenol | 10 parts |
| 5. (Bis(2-methoxyphenoxy)phosphinyl-methyl)-N-nitrosoamino-glycine, ethyl ester | 90 parts |
| Chloroform | 5 parts |
| Ethoxylated dinonyl phenol | 5 parts |
| 6. N-((diphenoxyphosphinyl)methyl)-N-nitroso-glycine, methyl ester | 75 parts |
| Butanol | 25 parts |
| 7. N-(di(4-methoxyphenoxyphosphinyl)-methyl)-N-nitroso-glycine, methyl ester | 75 parts |
| Ethoxylated oleyl alcohol | 25 parts |
| 8. N-(di(phenoxyphosphinyl)methyl)-N-nitroso-glycine | 75 parts |
| Acetonitrile | 15 parts |
| Ethoxylated cocoamine | 10 parts |
| 9. (Bis(2-methoxyphenoxy)phosphinyl-methyl)-N-nitrosoamino-glycine, ethyl ester | 75 parts |
| 1,2-Dimethoxyethane | 20 parts |
| Ethoxylated tallow amine | 5 parts |
| 10. N-((diphenoxyphosphinyl)methyl)-N-nitroso-glycine, methyl ester | 50 parts |
| Dimethylformamide | 50 parts |
| 11. N-(di(4-methoxyphenoxyphosphinyl)-methyl)-N-nitroso-glycine, methyl ester | 50 parts |
| Isopropyl dodecylbenzene sulfonate | 50 parts |
| 12. N-(di(phenoxyphosphinyl)methyl)-N-nitroso-glycine | 50 parts |
| Dimethylsulfoxide | 40 parts |
| Ethoxylated soybeanamine | 10 parts |
| 13. (Bis(2-methoxyphenoxy)phosphinyl-methyl)-N-nitrosoamino-glycine, ethyl ester | 50 parts |
| γ-butyrolactone | 25 parts |
| Triethanolamine dodecylbenzene sulfonate | 25 parts |
| 14. N-((diphenoxyphosphinyl)methyl)-N-nitroso-glycine, methyl ester | 50 parts |
| 1,1,1-Trichloroethane | 42 parts |
| Ethoxylated nonyl phenol | 8 parts |
| 15. N-(di(4-methoxyphenoxyphosphinyl)-methyl-N-nitroso-glycine, methyl ester | 25 parts |
| Chloroform | 75 parts |
| 16. N-(di(phenoxyphosphinyl)methyl)-N-nitroso-glycine | 25 parts |
| Chloroform | 70 parts |
| Ethoxylated tallow amine | 5 parts |
| 17. (Bis(2-methoxyphenoxy)phosphinyl-methyl)-N-nitrosoamine-glycine, ethyl ester | 25 parts |
| 1,1,1-Trichloroethane | 74 parts |
| Ethoxylated oleyl alcohol | 1 part |
| 18. N-((diphenoxyphosphinyl)methyl)-N-nitroso-glycine, methyl ester | 25 parts |
| Chloroform | 68 parts |
| Ethoxylated dinonyl phenol | 7 parts |
| 19. N-(di(4-methoxyphenoxyphosphinyl)-methyl)-N-nitroso-glycine, methyl ester | 10 parts |
| Chloroform | 90 parts |
| 20. N-(di(phenoxyphosphinyl)methyl)-N-nitroso-glycine | 10 parts |
| Methanol | 80 parts |
| Polyoxypropylene - polyoxyethylene block copolymer | 10 parts |
| 21. (Bis(2-methoxyphenoxy)phosphinyl-methyl)-N-nitrosoamino-glycine, ethyl ester | 10 parts |
| Ethanol | 88 parts |
| Polyoxyethylene (20) sorbitan-monolaurate | 2 parts |
| 22. N-((diphenoxyphosphinyl)methyl)-N-nitroso-glycine, methyl ester | 10 parts |
| Isopropanol | 72 parts |
| Polyoxyethylene sorbitan-monooleate | 18 parts |
| 23. N-(di(4-methoxyphenoxyphosphinyl)-methyl)-N-nitroso-glycine, methyl ester | 5 parts |
| Dimethylformamide | 95 parts |
| 24. N-(di(phenoxyphosphinyl)methyl)-N-nitroso-glycine | 5 parts |
| Acetonitrile | 90 parts |
| Ethoxylated tallow amine | 5 parts |
| 25. N-((diphenoxyphosphinyl)methyl)-N-nitroso-glycine, methyl ester | 5 parts |
| Ethanol | 94 parts |
| Ethoxylated tallow amine | 1 part |
| 26. N-(di(4-methoxyphenoxyphosphinyl)-methyl)-N-nitroso-glycine, methyl ester | 5 parts |
| Isopropanol | 80 parts |
| Ethoxylated cocoamine | 15 parts |

When operating in accordance with the present invention, effective amounts of the compounds or compositions of this invention are applied to the plants, or to soil containing the plants, or are incorporated into aquatic media in any convenient fashion. The application of liquid and particulate solid compositions to plants or soil can be carried out by conventional methods, e.g., power dusters, boom and hand sprayers and spray dusters. The compositions can also be applied from airplanes as a dust or a spray because of their effectiveness at low dosages. The application of herbicidal compositions to aquatic plants is usually carried out by adding the compositions to the aquatic media in the area where control of the aquatic plants is desired.

The application of an effective amount of the compounds or compositions of this invention to the plant is essential and critical for the practice of the present invention. The exact amount of active ingredient to be employed is dependent upon the response desired in the plant as well as such other factors as the plant species and stage of development thereof, and the amount of rainfall as well as the specific glycine employed. In foliar treatment for the control of vegetative growth, the active ingredients are applied in amounts from about 0.112 to about 56.0 or more kilograms per hectare. An effective amount for phytotoxic or herbicidal control is that amount necessary for overall or selective control, i.e., a phytotoxic or herbicidal amount. It is believed that one skilled in the art can readily determine from the teachings of this specification, including examples, the approximate application rate.

Although this invention has been described with respect to specific modifications, the details thereof are not to be construed as limitations, for it will be apparent that various equivalents, changes and modifications may be resorted to without departing from the spirit and scope thereof and it is understood that such equivalent embodiments are intended to be included herein.

What is claimed is:

1. A compound having the formula

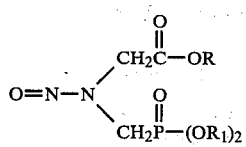

wherein R is a member of the class consisting of benzyl and lower alkyl and $R_1$ is a member of the group consisting of phenyl and lower alkoxy substituted phenyl.

2. A compound of claim 1 wherein $R_1$ is benzyl.
3. A compound of claim 1 wherein R is lower alkyl.
4. A compound of claim 3 wherein R is methyl or ethyl.
5. A compound of claim 4 wherein $R_1$ is phenyl.
6. A compound of claim 4 wherein $R_1$ is methoxyphenyl.
7. A compound of claim 6 which is methyl N-(di(4-methoxyphenoxy)phosphinylmethyl)-N-nitrosoglycinate.
8. A compound of claim 4 which is methyl N-((diphenoxyphosphinyl)methyl)-N-nitroso-glycinate.
9. A composition comprising a herbicidally effective amount of a compound of claim 1 and a herbicidally acceptable adjuvant.
10. A composition comprising a herbicidally effective amount of a compound of claim 2 and a herbicidally acceptable adjuvant.
11. A composition comprising a herbicidally effective amount of a compound of claim 3 and a herbicidally acceptable adjuvant.
12. A composition comprising a herbicidally effective amount of a compound of claim 4 and a herbicidally acceptable adjuvant.
13. A composition comprising a herbicidally effective amount of a compound of claim 5 and a herbicidally acceptable adjuvant.
14. A composition comprising a herbicidally effective amount of a compound of claim 6 and a herbicidally acceptable adjuvant.
15. A composition comprising a herbicidally effective amount of a compound of claim 7 and a herbicidally acceptable adjuvant.
16. A composition comprising a herbicidally effective amount of a compound of claim 8 and a herbicidally acceptable adjuvant.
17. A herbicidal method which comprises applying to plants a herbicidally effective amount of a compound of claim 1.
18. A herbicidal method which comprises applying to plants a herbicidally effective amount of a compound of claim 2.
19. A herbicidal method which comprises applying to plants a herbicidally effective amount of a compound of claim 3.
20. A herbicidal method which comprises applying to plants a herbicidally effective amount of a compound of claim 4.
21. A herbicidal method which comprises applying to plants a herbicidally effective amount of a compound of claim 5.
22. A herbicidal method which comprises applying to plants a herbicidally effective amount of a compound of claim 6.
23. A herbicidal method which comprises applying to plants a herbicidally effective amount of a compound of claim 7.
24. A herbicidal method which comprises applying to plants a herbicidally effective amount of a compound of claim 8.

* * * * *